United States Patent [19]

Vitolo

[11] Patent Number: 4,753,239

[45] Date of Patent: Jun. 28, 1988

[54] TRANSPARENT SHROUD FOR SUN BATHERS

[76] Inventor: Marguerite M. Vitolo, 447 Tenth Ave., New York, N.Y. 10001

[21] Appl. No.: 894,043

[22] Filed: Aug. 7, 1986

[51] Int. Cl.$^4$ ........................................... A61H 33/06
[52] U.S. Cl. .................... 128/372; 128/371; 128/373; 2/69.5
[58] Field of Search ............... 128/371, 372, 373; 135/91, 93, 102; 383/43, 66, 67; 2/69.5, 68; 36/8.1, 10

[56] References Cited

U.S. PATENT DOCUMENTS

| | | | |
|---|---|---|---|
| 2,478,765 | 8/1949 | Kim | 128/372 |
| 2,683,262 | 7/1954 | Foss | 2/69.5 |
| 3,955,227 | 5/1976 | Siegfried | 383/43 |
| 3,961,380 | 6/1976 | Garr | 128/373 |
| 4,161,180 | 7/1979 | Tiger | 128/372 |

FOREIGN PATENT DOCUMENTS

| | | | |
|---|---|---|---|
| 109851 | 4/1900 | Fed. Rep. of Germany | 135/93 |
| 13657 | 1/1897 | Switzerland | 135/93 |

*Primary Examiner*—Carl D. Friedman
*Assistant Examiner*—Michael Safavi
*Attorney, Agent, or Firm*—Charles E. Temko

[57] ABSTRACT

A transparent synthetic resinous shroud for protecting the skin of a sunbathing user to prevent drying of the skin while tanning. The shroud is full body length and has an elastic contractile opening permitting it to cover slightly more than one-half of the body of the reclining user. The shroud is provided with openings at certain areas to allow ventilation through the shroud, but prevents substantial evaporation of perspiration during the tanning period which would result in drying of the skin.

3 Claims, 1 Drawing Sheet

U.S. Patent    Jun. 28, 1988    4,753,239
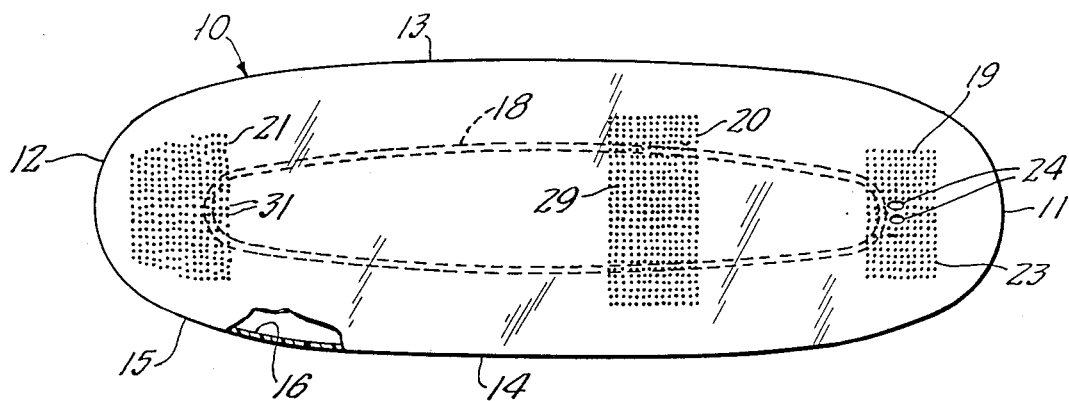
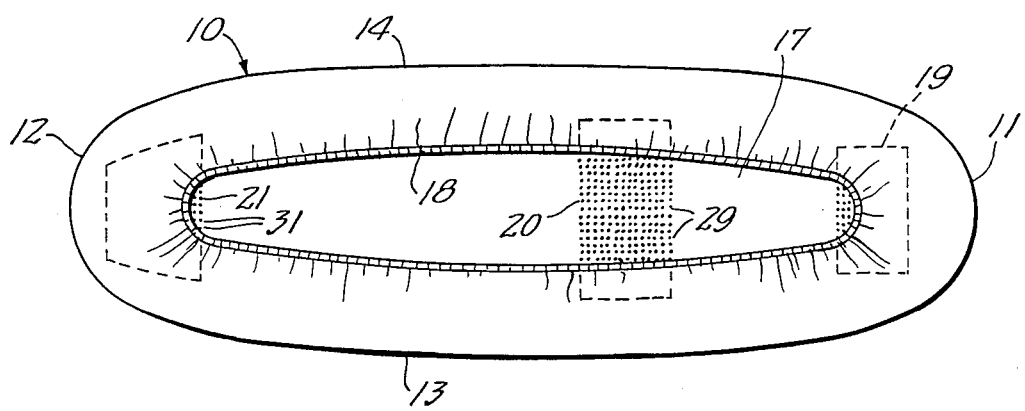
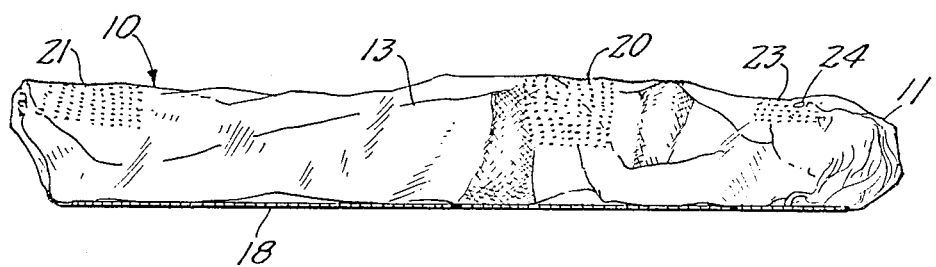

TRANSPARENT SHROUD FOR SUN BATHERS

BACKGROUND OF THE INVENTION

This invention relates generally to the field of health care, and more particularly to an improved means and method for tanning the skin of a user without the usual accompanying drying of the skin as a result of loss of moisture.

Particularly in the case of older persons, the most serious skin problem resulting from exposure to the sun is the loss of moisture resulting from rapid evaporation of perspiration.

It is known in the art to use various suntan lotions which afford protection against ultraviolet light and thereby diminish execessive sunburn. However, such lotions do not retard evaporation from the skin. It is also known to provide and use a wide variety of oil based creams which impart an oily coating to the surface of the skin. Unfortunately, such coatings do not prevent the drying of the skin beneath the oily coating, since perspiration tends to evaporate through the coating under the heat of the sun.

SUMMARY OF THE INVENTION

Briefly stated, the invention contemplates the provision of an improved body shroud or cover for use by a reclining user during exposure to the sun which will permit controlled tanning of the skin while effectively limiting the degree of moisture evaporation from the surface thereof during the tanning process. To this end, the shroud is in the form of an elongated cap-like envelope having an axially oriented contractile opening enabling the same to be slipped over the head and feet of the user and cover the exposed half of the body facing the rays of the sun. The shroud is provided with openings through which the user can breath, and vents in the area of the feet and lower torso for limited ventilation. When the user turns over to the opposite side of the body, the device is used to cover the newly exposed areas to be tanned. Preferably, the shroud is formed from transparent thin vinyl material with the expandable opening having an elastic border, consistent with limited reusability and low cost of manufacture.

BRIEF DESCRIPTION OF THE DRAWING

In the drawing, to which reference will be made in the specification, similar reference characters have been employed to designate corresponding parts throughout the several views.

FIG. 1 is a top plan view of an embodiment of the invention.

FIG. 2 is a bottom plan view thereof.

FIG. 3 is a side elevational view thereof showing the device in use.

DETAILED DESCRIPTION OF THE DISCLOSED EMBODIMENT

In accordance with the invention, the device, generally indicated by reference character 10, is in the form of an elongated synthetic resinous shroud having first and second oppositely disposed ends 11 and 12, respectively, and first and second sides 13 and 14, respectively. The shroud is made of transparent or translucent synthetic resinous material such as vinyl, and is bounded by an outer surface 15 and an inner surface 16 which meet at a generally ovate contractile opening 17, the periphery of which is provided with an elastic binding 18 enabling the device to maintain itself in position upon a reclining user.

Extending between the inner and outer surfaces is an upper ventilated area 19 which, in use, overlies the face of a user. A medially positioned ventilated area 20 overlies the lower torso of the user, and a lower ventilated area 21 overlies the feet of the user. The area 19 includes an area of small perforation 23 as well as a pair of larger openings 24 which may be positioned adjacent the nose of the user to facilitate breathing. During use, a substantial amount of relatively cool air will travel through the opening 17, and between the body of the user and the inner surface 16, and when exhaled, this air can pass through the larger openings 24.

The area 20 can be of generally rectangular shape, and is provided with relatively small perforations 29 to allow for some degree of passage of moisture vapor, so that the user does not have a sticky feeling while tanning. This is equally true of the third area 21 which has small perforations 31.

During use, the user places himself in a prone position and can most conveniently don the shroud by placing his feet inside the shroud at the second end 12, and then pass his body through the stretched elongate opening so that the first end 11 may enclose his head. The opening is then allowed to contract which will bring the shroud to the position shown in FIG. 3. When the tanning procedure on the front part of the body of the user has progressed to the desired point, the body may be turned within the shroud, using external assistance, if necessary, and the tanning procedure continued. In this case, the face of the user will be facing downwardly, and the nose of the user can project through the upper end of the contractile opening 17. During the tanning procedure, a limited amount of moisture will evaporate from the body of the user, but excess drying is prevented, so the skin may remain moist. While tanning takes place, the skin is prevented from flaking and wrinkling, due to excessive drying.

With normal usage, the device, although made of relatively thin and inexpensive synthetic resinous materials, can be used for a plurality of tanning operations, and should the same become ripped, it can be temporarily patched using pressure-sensitive tape. Upon completion of each use, it is desirable to allow the inner surface 16 to dry, to facilitate donning for subsequent use. However, since the total cost of manufacture can be of a relatively low order, the device can be conveniently discarded after approximately one-half dozen uses.

I wish it to be understood that I do not consider the invention limited to the precise details of structure as shown and set forth in this specification, for obvious modifications will occur to those skilled in the art to which the invention pertains.

I claim:

1. A shroud for use in sunbathing by a user having a given height and transverse width, said shroud comprising: an elongated cap-like body of transparent synthetic resinous material having a principal axis and axially aligned ends, said body having an effective length substantially equal to said height of said user, and an effective width substantially equal to said transverse width of said user; said body defining an elongated opening extending substantially the length of said body, and having an elastic contractile binding thereon bordering the pheriphery of said opening; said body having a perforate area adjacent one end thereof adapted to be positioned over the face of said user when said shroud is in use.

2. A shroud in accordance with claim 1, further characterized in at least one additional perforate area disposed medially with respect to the axially aligned ends of said body.

3. A shroud in accordance with claim 1, further characterized in at least two additional perforate areas medially disposed with respect to the axially disposed ends of said body.

* * * * *